(12) United States Patent
Stier et al.

(10) Patent No.: US 6,770,264 B2
(45) Date of Patent: *Aug. 3, 2004

(54) CHEWING GUM COMPOSITIONS COMPRISING DIGLYCEROL

(75) Inventors: Roger E. Stier, Clifton, NJ (US); Daniel Carey, Darien, CT (US); Douglas P. Fritz, Wilmington, NC (US)

(73) Assignee: Noville, Inc., South Hackensack, NJ (US)

( * ) Notice: Subject to any disclaimer, the term of this patent is extended or adjusted under 35 U.S.C. 154(b) by 63 days.

This patent is subject to a terminal disclaimer.

(21) Appl. No.: 10/338,464

(22) Filed: Jan. 8, 2003

(65) Prior Publication Data

US 2003/0095929 A1 May 22, 2003

Related U.S. Application Data

(63) Continuation-in-part of application No. 10/266,493, filed on Oct. 8, 2002, which is a continuation-in-part of application No. 10/008,844, filed on Nov. 13, 2001, now abandoned.

(51) Int. Cl.[7] .................................................. A61K 9/68
(52) U.S. Cl. ............................. 424/48; 424/440; 426/3; 426/6; 264/148; 264/151
(58) Field of Search ...................... 424/48, 440; 426/3, 426/6; 264/148, 151

(56) References Cited

U.S. PATENT DOCUMENTS

| | | |
|---|---|---|
| 2,584,307 A | 2/1952 | Tice |
| 2,975,102 A | 3/1961 | Matsumura et al. |
| 3,523,130 A | 8/1970 | Jones et al. |
| 3,840,656 A | 10/1974 | Kalopissis et al. |
| 3,873,686 A | 3/1975 | Beekman |
| 3,876,758 A | 4/1975 | Beekman |
| 4,556,557 A | 12/1985 | Reichert |
| 4,726,943 A * | 2/1988 | Klueppel et al. ............. 424/54 |
| 4,829,092 A * | 5/1989 | Nelson et al. ............. 514/738 |
| 4,960,953 A * | 10/1990 | Jakobson et al. ........... 568/621 |
| 4,973,763 A * | 11/1990 | Jakobson et al. ........... 568/619 |
| 5,041,688 A * | 8/1991 | Jakobson et al. ........... 568/620 |
| 5,342,617 A | 8/1994 | Gold |
| 5,368,847 A | 11/1994 | Brunetta et al. |
| 5,449,551 A | 9/1995 | Taniguchi |
| 5,456,863 A | 10/1995 | Bergmann |
| 5,474,776 A | 12/1995 | Koyanagi et al. |
| 5,538,720 A | 7/1996 | Jendryssek-Pfaff et al. |
| 5,650,166 A | 7/1997 | Ribier et al. |
| 5,709,849 A | 1/1998 | Ito et al. |
| 5,750,120 A | 5/1998 | Miguel-Colombel |
| 5,874,092 A * | 2/1999 | Roulier et al. ............. 424/401 |
| 5,902,590 A | 5/1999 | Thomas et al. |
| 5,935,384 A | 8/1999 | Taniguchi |
| 5,989,573 A | 11/1999 | Remy |
| 6,001,341 A | 12/1999 | Genova et al. |
| 6,036,968 A * | 3/2000 | Roulier et al. ............. 424/401 |
| 6,042,844 A | 3/2000 | Ishida et al. |
| 6,045,781 A | 4/2000 | Bungard et al. |
| 6,117,434 A | 9/2000 | Oyama et al. |
| 6,126,928 A | 10/2000 | Swaile |
| 6,146,647 A | 11/2000 | Aoyama et al. |
| 6,180,124 B1 | 1/2001 | Ohta et al. |
| 6,206,902 B1 | 3/2001 | Morikane |
| 6,221,382 B1 | 4/2001 | Ishida et al. |
| 6,419,962 B1 | 7/2002 | Yokoyama et al. |
| 6,569,439 B1 | 5/2003 | Stier |
| 6,579,543 B1 | 6/2003 | McClung |
| 2003/0044359 A1 | 3/2003 | Wuelknitz et al. |

FOREIGN PATENT DOCUMENTS

| | | |
|---|---|---|
| DE | 196 24 870 A1 | 1/1998 |
| DE | 100 15 662 A1 | 10/2001 |
| WO | PCT/US96/02257 | 9/1996 |

OTHER PUBLICATIONS

Product Data Sheet—Diglycerol—Solvay Interox web page (1999).
Abstract of Kapsalis et al., NATO ASI Ser. E. 90: 481–496 CAPLUS:576212 (1985) CA. 103:176212, (1985).
Abstract of Babayan, Food Prod. Develop. 2(2); 58, 60–61–64 CAPLUS 418091 (1968) CA.69:18091.
European Search Report dated Feb. 27, 2003.
Kapsaus et al Nato asi Ser. Ser. E. 90:481–496 CAPLUS:576212 (1985) CA. 103:176212, 1985.*
Babayan Food Prod. Develop. 2(2): 58, 60–61–64 CAPLUS: 418091 (1968) CA. 69: 18091, 1968.*
Product Data Sheet—Diglycerol—Solvay Interox web page "is a humectant in personal care products" Apr. 2, 2001.

* cited by examiner

*Primary Examiner*—Frederick Krass
(74) *Attorney, Agent, or Firm*—Norris, McLaughlin & Marcus

(57) ABSTRACT

The invention relates to oral care compositions such as toothpaste, gels, tooth powders, mouthwashes, mouth rinses, gums, such as chewing gum, mouth sprays and lozenges comprising diglycerol. The diglycerol is used as a humectant in the compositions. The compositions may further comprise water, flavoring agents, active compounds, emulsifier, alcohol, sweeteners, thickening agents, surfactants, suspending agents, astringent and toning drug extracts, flavor correctants, abrasives or polishes, deodorizing agents, preservatives, flavoring buffers, whitening agents, wound-healing and inflammation inhibiting substances, colorants, dyes, pigments, abrasives, polishes, antimicrobial agents, pH buffers and other additives and fillers.

25 Claims, 3 Drawing Sheets

CHEWING GUM COMPOSITIONS COMPRISING DIGLYCEROL

CROSS-REFERENCE TO RELATED APPLICATIONS

This application is a continuation-in-part of U.S. patent application Ser. No. 10/008,844 filed Nov. 13, 2001, which is now abandoned. A separate continuation-in-part application of U.S. patent application Ser. No. 10/008,844 is also currently pending. (U.S. Ser. No. 10/266,493, filed Oct. 8, 2002).

BACKGROUND OF THE INVENTION

1. Field of the Invention

The invention relates to oral care compositions, such as toothpaste, gels, mouthwashes, mouth rinses, chewing gums of any type including confectionary gum, mouth sprays and lozenges, comprising diglycerol. The diglycerol provides humectant and emollient properties to the compositions.

2. The Prior Art

Oral malodor, plaque, gingivitis, periodontal disease, and discoloration of the teeth, are all undesirable conditions that affect many people. Malodor of the oral cavity is also known as halitosis or bad breath and it is generally believed that the cause of this condition is due to the presence of anaerobic bacteria, especially gram-negative anaerobic bacteria, in the mouth. These bacteria will generate volatile sulfur compounds (VSC), which are known to cause breath malodor.

Three chemical compounds cause some breath malodor, specifically, hydrogen sulfide (H—S—H), methyl mercaptan ($CH_3$—S—H) and dimethyl sulfide ($CH_3$—S—$CH_3$). These compounds result from the degradation of epithelial cells and bacteria in the oral cavity. The polypeptide chains of the epithelial cell walls are composed of a series of amino acids including cysteine and methionine, which contain sulfur side chains. The death of microorganisms or epithelial cells results in degradation of the polypeptide chains into their amino acid components, especially cysteine and methionine. Cysteine and methionine are precursors to the formation of VSC.

Oral malodor not only comes from the posterior dorsal surface of the tongue but also from periodontal pockets. A person with gingivitis or periodontal disease may have increased oral malodor from disintegrated epithelial cells. Epithelial cells turn over faster if inflammation is present. Therefore, a larger number of these dead epithelial cells remain in the oral cavity and will degrade into the malodorous compounds. In addition VSC will also alter the epithelial barrier, permitting penetration of the barrier by antigenic substances.

Oral care compositions, such as toothpaste, gels, mouthwashes, mouth rinses, chewing gums, mouth sprays and lozenges, are directed, completely or in part, towards alleviating the conditions in the mouth which cause malodor, generally by physical, means, such as brushing teeth with a dentifrice or chewing gum, or by chemical means, such as masking malodor. The effectiveness of oral care compositions is generally perceived as a function of both 1) the ability of the active components of the oral care composition in attacking the conditions which bring about oral malodor, plaque, gingivitis, periodontal disease, and discoloration of the teeth and 2) prolonged smooth lasting effect and long lasting flavor and cooling characteristics in the mouth perceived by the user. Dentifrice manufacturers and chewing gum manufacturers are constantly seeking ways to prolong the smooth lasting effect and flavor and cooling characteristics of oral care compositions and chewing gum.

Humectants and emollients absorb and promote the retention of moisture from the air. Traditional humectants in oral care compositions are glycerol, sorbitol or glycols. One of the more common humectants used in oral care compositions is glycerol that absorbs moisture in the mouth, which serves to diminish the overall smooth lasting effect perceived by the user.

Flavor and cooling effects result primarily from the incorporation of flavoring and cooling agents in the oral care compositions and chewing gum. The objective in increasing the flavoring and cooling effect of an oral care composition, such as chewing gum, is to increase the time that the flavoring and/or cooling agents remain effective after the product is applied by the consumer. Expensive and cost prohibitive methods of encapsulation are generally the means of achieving this objective. A formulation which efficiently enhances the flavoring and cooling effects of oral care compositions such as chewing gum, without costly means like encapsulation has long eluded the industry.

Diglycerol has, to the inventor's knowledge, not been used in oral care compositions, and chewing gum, as a humectant or emollient, or otherwise. For example, U.S. Pat. No. 4,726,943 describes anti-caries compositions comprising phosphoric acid esters of alkoylated polyols, including diglycerol, as an active component with low molecular weight polyethylene glycols, glycerol and sorbitol as humectants in the composition. Also, U.S. Pat. No. 5,395,290 concerns a process for preparing a rosin ester that is said to be useful in a gum base, among other things, wherein disproportionated rosin may be esterified with an alcohol, including diglycerol among others, and dehydrogenated. U.S. Pat. No. 4,514,422 describes a chewing gum containing gum base, at least one sugar alcohol and from about 8% to about 18% glycerin, but containing no more than 2% by weight water in any form.

The inventors have discovered that incorporation of diglycerol as a humectant and/or emollient in a chewing gum composition provides long-lasting flavor and sweetening effects than experienced with chewing gum comprising conventional humectants. The diglycerol may be used with other humectants and emollients in the compositions and can replace some or all of the traditional and conventional humectant components of chewing gum compositions. The chewing gum compositions comprising diglycerol have enhanced prolonged smooth lasting effect and long lasting flavor, sweetening and cooling effect due in part to the characteristics of the diglycerol molecule and its interaction with flavoring agents, which may incorporate cooling agents, after application of the composition.

Chewing gum can be made on a batch basis using double sigma or double "Z" design mixers, and on a continuous basis using a screw type mixer. These processes are known in the art and are described, for example, in booklet titled "GUM TECHNOLOGY" compiled by CAFOSA GUM, S.A., Barcelona, Spain which is incorporated herein by reference. Generally, after mixing, the chewing gum is formed into individual pieces by processes involving an extrusion step, followed by a series of steps to cool, shape and size the pieces by mechanical means. These processes were developed for chewing gums containing sugar and corn syrup, and not for chewing gums that are known as sugar-free gums that use sugarless sweeteners, like polyols such as sorbitol, xylitol and maltitol syrups. It should be appreciated by one skilled in the art that sugar-free chewing gums are difficult to process because the polyols do not provide the chewing gum with good body and stretching ability. We have discovered that inclusion of diglycerol in chewing gum enables the manufacture of sugar-free chewing gum using a process substantially similar to that used for the manufacture of gum comprising sugar or corn syrup, that does not have the processing difficulties experienced with conventional sugar-free formulations that do not comprise diglycerol.

In the present Specification, all parts and percentages are on a weight/weight basis unless otherwise specified.

SUMMARY OF THE INVENTION

The invention pertains to oral care compositions and chewing gum compositions, comprising diglycerol. The diglycerol is a humectant and/or emollient in the composition and can be used with other humectants and emollients. The compositions can further comprise other ingredients, additives and fillers. The invention also pertains to an improved process for making sugar-free chewing gum. The chewing gum compositions of the invention involve all types of chewing gum whether or not the chewing gum provides oral care to the user or is merely a confectionary.

DETAILED DESCRIPTION OF THE INVENTION

Figure 1:
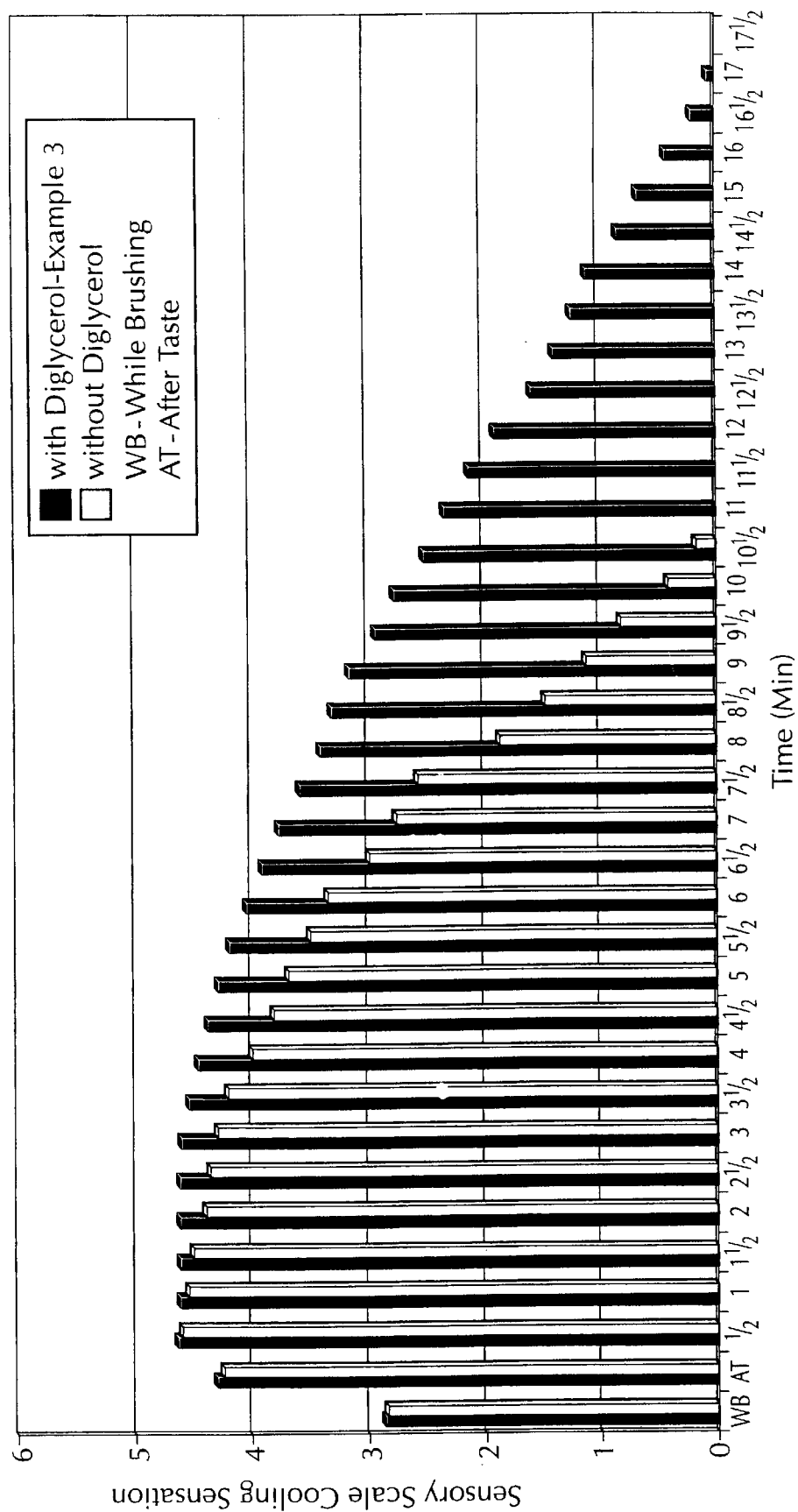
FIG. 1. is a graph depicting cooling perception over time for on oral care composition of the invention comprising diglycerol and a comparative oral care composition that does not comprise diglycerol.

The oral care compositions may comprise about 10.0% to about 70.0% humectants, comprising at least diglycerol, and in the case of chewing gum, the oral care compositions comprise from about 0.1% to about 25% humectants. The humectant used in the system may comprise from about 5% to 100% diglycerol (based on the total weight of humectant material in the composition) and up to about 95% other humectants (based on the total weight of humectant material in the composition). The other humectants include substances selected from the group consisting of edible polyhydric alcohols and polyols such as glycerol, propylene glycol, propylene glycol glycerol, polyethylene glycol, isomalt, xylitol, maltitol, sorbitol, mannitol and the like, and combinations thereof. Diglycerol is a polyol consisting of two molecules of glycerol bonded by an ether linkage and is available from Solvay Interox, Inc., Houston, Tex. U.S.A. Polyhydric alcohols and polyols are generally available from SPI Polyols, Inc., New Castle, Del., U.S.A., and glycerol is available from many sources including Rierden Chemicals Trading Company, Libertyville, Ill., U.S.A.

The oral care compositions, including chewing gum, may also comprise from about 5.0% to about 80.0% water, about 0.05% to about 2.0%, and up to about 3.0%, flavoring agents, and about 0.05% to about 10.0% active compounds. In addition, the oral care compositions may comprise other ingredients selected from the group consisting of emulsifier, alcohol, sweeteners, thickening agents, surfactants, astringent and toning drug extracts, flavor correctants, abrasives or polishes, deodorizing agents, preservatives, flavoring buffers, whitening agents, wound-healing and inflammation inhibiting substances, colorants, dyes, pigments, abrasives, polishes, antimicrobial agents, pH buffers, and the like and combinations thereof, as well as other additives and fillers, the selection and amount of which will depend on the nature of the oral care composition.

Flavoring agents useful for the invention are any food grade or pharmaceutically acceptable flavoring agent, and the specific flavoring agents will depend on the type of oral care composition. Preferably, the flavoring agent comprises natural flavoring oils, including those selected from the group consisting of oil of peppermint, oil of wintergreen, oil of spearmint, clove bud oil, parsley oil, eucalyptus oil, oil of lemon, oil of orange and the like. Combinations of oils can also be used. The flavoring agents may comprise compounds selected from the group consisting of menthol, menthane, anethole, methyl salicylate, eucalyptol, cassia, 1-methyl acetate, sage, eugenol, oxanone, alpha-irisone, marjoram, lemon, orange, propenyl guaethol acetyl, cinnamon, vanilla, thymol, linalool, cinnamaldehyde glycerol acetal and the like, and combinations thereof. The flavoring agent may comprise combinations of natural flavoring oils and other flavoring agents such as the compounds identified above. Also, the flavoring agent may comprise cooling agents such as menthol, N-substituted p-menthane-3-carboxamides (such as N-ethyl p-methane-3-carboxamide), 3,1-methoxy propane 1,2-diol and the like, or combinations thereof.

The active compounds of the oral care composition will depend on the nature and use of the composition. In general, the active compounds for oral care compositions mask oral malodor, attack the chemicals that bring about the oral malodor, kill or inhibit growth of the bacteria in the mouth that cause breath malodor or halitosis, attack tartar, remove dirt from the teeth and mouth and/or whiten teeth. For example, in embodiments of the invention where the oral care compositions are in the form of mouthwashes, mouth rinses, chewing gums, mouth sprays, lozenges and the like, the active components include oral hygiene actives, antibacterial substances, desensitizing agents, antiplaque agents and combinations thereof, such as those selected from the group consisting of chlorine dioxide, fluoride, alcohols, triclosan, domiphen bromide, cetyl pridinium chlorine, calcium lactate, calcium lactate salts and the like, and combinations thereof. In embodiments of the invention where the oral care compositions are in the form of dentifrices, such as toothpaste, gels, and the like, the active components include oral hygiene actives, antibacterial substances, desensitizing agents, antiplaque agents and combinations thereof, such as those selected from the group consisting of sodium fluoride, stannous fluoride, sodium monofluorophosphate, triclosan, cetyl pyridium chloride, zinc salts, pyrophosphate, calcium lactate, calcium lactate salts, 1-hydroxyethane-1,2-diphosphonic acid, 1-phosphonopropane-1,2,3-tricarboxylic acid, azacycloalkane-2,2-diphosphonic acids, cyclic aminophosphonic acids and the like, and combinations thereof.

Chewing gum generally comprises a neutral and tasteless water-insoluble masticatory chewing gum base and one or more water-soluble non-masticatory ingredients mixed therein. The water-soluble portions of the chewing gum dissipate over a period of time, and the gum base portion is retained during mastication.

Chewing gum bases are defined according to Federal regulation set forth in 21 C.F.R. §172.615, which is incorporated herein by reference. Chewing gum base generally comprises natural gums and/or synthetic elastomers and resins. Natural gums comprise both elastomers and resins. Natural gums useful for chewing gums include, but are not limited to, those selected from the group consisting of chicle, jelutong, sorva, nispero tunu, niger gutta, massaranduba belata, and chiquibul, and also natural rubber such as smoked or liquid latex and guayule, and combinations of these. Synthetic elastomers useful for chewing gum are those selected from the group of polyisobutylene, isobutylene-isoprene copolymer, styrene butadiene copolymer, polyvinylacetate, polyvinylacetate polyethylene copolymers, polyvinylacetate polyvinyl laureate copolymers and the like, and mixtures or combinations thereof. Chewing gum bases also generally comprise elastomer solvents including, but are not limited to, those selected from the group of natural rosin esters such as glycerol esters of partially hydrogenated rosin, glycerol esters of polymerized rosin, glycerol esters of partially dimerized rosin, glycerol esters of rosin, pentaerythritol esters of partially hydrogenated rosin, methyl esters of partially hydrogenated rosin, pentaerythritol esters of rosin; synthetic resins such as terpene resins derived from alpha-pinene, beta-pinene, and/or d-limonene; and the like, and combinations thereof. The specific elastomer solvents may vary depending on the particular application, and on the types of elastomer that are used. Chewing gum base may further include fat, such as oils from either hydrogenated and partially hydrogenated vegetable oils or animal fats, such as those selected from the group consisting of soybean oil, palm oil, sunflower oil, cottonseed oil, cocoa butter, lard and tallow, and the like, and combinations thereof. Waxes, including petroleum waxes such as paraffin and microcrystalline wax, natural waxes such as beeswax, candellia, carnauba, rice bran wax and polyethylene wax, and combinations of these waxes, may also be a component of the chewing gum base. The chewing gum base may also comprise from about 0.01% to about 0.1%, by weight of the chewing gum base, of an antioxidant ingredient such as butylated hydroxytoluene, butylated hydroxyanisole, propyl gallate, tocopherols or combinations thereof. Chewing gum base typically also contains a filler component such as calcium carbonate, magnesium carbonate, talc, dicalcium phosphate and the like; softeners, including glycerol monostearate and glycerol triacetate; and optional ingredients such as antioxidants, colors and emulsifiers such as lecithin. The chewing gum composition will generally comprise about 5% and about 95% chewing gum base, preferably about 10% to about 50% chewing gum base and most preferably about 20% to about 30% chewing gum base.

The chewing gum formulation comprises from about 0.1% to about 25% humectants. The chewing gum compositions may preferably comprise from about 0.3% to about 6% humectants, most preferably from about 0.5% to about 4%. The humectant used in the chewing gums described herein comprises at least diglycerol, such as from about 5% to 100% diglycerol (based on the total weight of humectant material in the composition) and up to about 95% other humectants (based on the total weight of humectant material in the composition). The humectant in the chewing gum composition may consist essentially of or consist of diglycerol. The humectant may, in addition to enhancing the lasting effect of the flavoring and sweetening agents, provide softness to the chewing gum to enhance the ability to chew the chewing gum and also improves mouth feel. We have discovered that the use of diglycerol provides enhanced mouth feel compared to other ingredients conventionally used to soften the chewing gum base. We have further found that the diglycerol imparts greater elasticity to sugar-free chewing gum formulations, compared to sugar-free chewing gums that do not comprise diglycerol, which facilitates and improves sugar-free chewing gum processing. Although not wishing to be bound to any theory, the diglycerol in the chewing gum formulation will not pick up moisture from the air as quickly as other humectant material, such as glycerol, thereby allowing more diglycerol to be used in the gum compared to the amount of conventional humectant, like glycerol, yielding softer chewing gum. This is particularly beneficial for stick chewing gum.

The chewing gum may further include one or more antiplaque or anticalculus agents, which can reduce or prevent the formation of plaque deposits and/or calculus on teeth. There are many known antiplaque and anticalculus compositions in the art, which may be incorporated into a chewing gum product of the invention. These may include, for example, encapsulated or nonencapsulated alkali metal bicarbonate or various polyphosphate compounds. Antiplaque and anticalculus compositions may be present in the chewing gum in an amount from about 1% to about 30%, however those skilled in the art may modify these amounts without departing from the spirit of the invention to further promote dental health and hygiene.

The chewing gum may also include fluoridating ingredients for the prevention of dental caries, which are typically present in an amount sufficient to release up to about 500 ppm, preferably about 25 ppm to 300 ppm by weight of fluoride ion. Generally about 0.005% to about 3.0% by weight of such compound is present. Fluoridating agents include, for example, alkali metal fluoride, ammonium fluoride, stannous fluoride, stannous chlorofluoride, potassium stannous fluoride, alkali metal monofluorophosphate, ammonium monofluorophosphate, and the like.

The chewing gum may further comprise an abrasive ingredient in an amount from about 1% to about 20% of the chewing gum to provide a dentifrice cleaning action, in addition to other-antiplaque or anticalculus agents. The abrasives and polishes discussed herein with respect to dentifrice compositions of the present invention may be incorporated into the chewing gum. Also, the preservatives and anti-microbial agents discussed above with respect to the dentifrice compositions may be included in the chewing gum of the invention.

The chewing gum may further comprise ingredients selected from the group consisting of water-soluble and usually sweet non-masticatory bulking agents, coloring agents, and/or plasticizing agents. Water-soluble bulking agents may include bulk sweeteners, high-potency sweeteners, flavorants, softeners, emulsifiers, colorants, fillers, antioxidants and combinations thereof, and other constituents which contribute desirable attributes.

The bulking agent can comprise between about 5% and about 70% of a bulking sweetener. Bulking sweeteners can consist of sugar and/or sugarless constituents. Sugar sweeteners include saccharides such as sucrose, dextrose, maltose, dextrin, dried invert sugar, fructose, levulose, galactose, corn syrup solids, and the like, and combinations thereof. Sugarless sweeteners include polyhydric alcohols such as sorbitol, mannitol, xylitol, hydrogenated starch hydrolysates, maltitol, isomalt, erythritol, and the like and combinations thereof. A high potency sweetener ingredient can be utilized alone or in combination with a bulk sweetener. High potency sweeteners include aspartame, saccharin, cyclamate, thaumatin, dihydrochalcones, acesulfame K compounds, sucralose, neotame, alitame, glycyrrhizin, and stevioside and the like, and combinations thereof. By way of example and not limitation as to the nature and type of high potency sweetener that can be used, TWINSWEET® artificial sweetener available from Holland Sweetener Company, Gaeleen, Netherlands may be used. Chewing gum compositions may comprise about 0.025% to about 2% high intensity sweeteners. Sugar-free chewing gums generally refer to chewing gum that does not comprise sugar sweeteners or sweetening agents, i.e. the sugar-free chewing gum comprises sugarless sweeteners.

The chewing gum also comprises a flavoring agent, such as those discussed herein with respect to the oral care compositions of the invention, in general, and include any flavoring or sweetening material used conventionally in the art. In addition to those set forth above with respect to suitable flavoring agents in general, examples of flavorants suitable for the chewing gum include flavoring oils, e.g., oils of spearmint, peppermint, wintergreen, sassafras, clove, sage, anise, eucalyptus, marjoram, cinnamon, lemon, orange, methyl salicylate and the like. The flavorant in the chewing gum composition may further comprise sweetening agents, such as those selected from the group consisting of sucrose, lactose, maltose, sorbitol, xylitol, sodium cyclamate, perillartine, aspartyl phenyl alanine methyl ester, and saccharine and combinations thereof. The flavorant may comprise from about 0.1% to about 5% or more of the chewing gum composition.

The chewing gum may further comprise from about 0.001% to about 0.2% of colorants, such as FD&C-type dyes and lakes, including those discussed herein with respect to the dentifrice and mouthwash embodiments of the invention. The colorant can be in the form of particles which give the chewing gum matrix a speckled appearance. The speckled effect also can be incorporated in a surface coating, such as the coating on dragée chewing gum products.

Typical mouthwash, mouth rinse, mouth spray and lozenge compositions will comprise about 30% to about 80% water, about 2% to about 35% humectant comprising at least diglycerol, about 1% to about 10% active compounds, about 0.01% to about 0.50% of at least one sweetener, about 0.01% to about 0.50% of at least one thickening agent or binder which may be dispersed in about 2.5% to about 10% of a carrier, such as glycerol, polyethylene glycol (PEG-400) or combinations thereof, about 0.03% to about 3% of at least one surfactant and about 0.01% to about 1% of at least one flavoring agent. Optionally, the typical mouthwash, mouth rinse, mouth spray, chewing gum or lozenge compositions can comprise about 0.01% to about 1.0% colorants, which includes dyes and pigments and about 0.01% to about 1.0% clouding agents. The compositions may further comprise about 0.01% to about 1.0% titanium dioxide (such as U.S.P. grade available from Whittaker, Clark & Daniels, South Plainfield, N.J., U.S.A.).

Any food grade and/or pharmaceutically acceptable sweetener maybe used in the mouthwash, mouth rinse, mouth spray or lozenge compositions, including saccharin, fructose, xylitol, saccharin salts, thaumatin, aspartame, D-tryptophan, dihydrochalcones, acesulfame K and cyclamate salts, especially sodium cyclamate and sodium saccharin, and combinations thereof. Food grade and/or pharmaceutically acceptable coloring agents, or colorants, as would be understood to one skilled in the art, can be used in these compositions, including Food, Drug and Cosmetic- (FD&C) colorants such as primary FD&C Blue No. 1, FD&C Blue No. 2, FD&C Green No. 3, FD&C Yellow No. 5, FD&C Yellow No. 6, FD&C Red No. 3, FD&C Red No. 33 and FD&C Red No. 40 and lakes FD&C Blue No. 1, FD&C Blue No. 2, FD&C Yellow No. 5, FD&C Yellow No. 6, FD&C Red No. 2, FD&C Red No. 3, FD&C Red No. 33, FD&C Red No. 40 and combinations thereof. Like colorants and dyes may also be used.

Any food grade or pharmaceutically acceptable thickening agent or binder may be used in the mouthwash, mouth rinse, mouth spray or lozenge compositions. The thickening agent or binder may be dispersed in a carrier, such as glycerol, polyethylene glycol or combinations thereof (thickening agent/carrier dispersion). Thickening agents and binders are those selected from the group consisting of xanthan gum, polymeric polyester compounds, natural gums (e.g. gum karaya, gum arabic, gum tragacanth), carrageenan, hydroxymethyl cellulose, methyl cellulose, carboxymethylcellulose, arrowroot powder, starches, particularly corn starch and potato starch and the like, and combinations thereof. The thickening agent or binder may be used with or without a carrier, however, when a carrier is used, up to about 5% thickening agent or binder, preferably from about 0.1% to about 1.0%, is combined with about 95.0% to about 99.9% carrier, preferably about 99.0% to about 99.9%, based on the total weight of the thickening agent/carrier combination.

Clouding agents that may be used in the mouthwash, mouth rinse, mouth spray or lozenge compositions include those selected from the group consisting of calcium citrate, esters of wood rosin, vegetable gum emulsion, caprylic/capric triglycerides, certain gums like guar gum or gum arabic and high-stability oils. Caprylic/capric triglyceride clouding agents are available from Stepan Company, Northfield, Ill., U.S.A. under the trade name NEOBEE®.

In another embodiment of the invention, the oral care composition is in the form of a dentifrice, such as toothpaste or gels. Toothpaste and gels are generally understood to be paste-like or gel-like preparations that are applied directly to the teeth generally by brushing, and dentifrices may be a combination of pastes and gels, as well as combinations of gels or toothpaste with mouthwashes or mouth rinses.

Chewing gums and lozenges may also be used as dentifrices provided that these include the active ingredients normally associated with dentifrice compositions. The chewing gums and lozenges of the invention also comprise the humectant having at least diglycerol.

The dentifrice composition will generally comprise from about 5% to about 20% water, about 5% to about 75% humectant comprising at least diglycerol, about 0.25% to about 3.0% of at least one thickening agent or binder which may be dispersed in about 2.5% to about 10% of a carrier, such as glycerol, polyethylene glycol (PEG-400), or combinations thereof, about 0.01% to about 0.05% sweeteners, about 5% to about 40% abrasives and polishes, about 0.5% to about 3.0% surfactants, about 0.01% to about 10.0% active compounds which may include oral hygiene actives, antibacterial substances, desensitizing agents, antiplaque agents and combinations thereof, and about 0.25% to about 3.0% flavoring agents. The dentifrice compositions may also comprise fillers and additives, such as about 0.05% to about 1.0% preservative and/or antimicrobial agents, about 0.50% to about 10.0% buffers, about 0.05% to about 5.0% wound healing and inflammation-inhibiting substances, about 0.01% to about 2.0% colorants, such as colors, dyes or particles for special effects, and from about 0.05% to about 10.0% whitening agents, such as hydrogen peroxide and pyrophosphates.

The thickening agent or binder for the dentifrice, may be selected from the group consisting of finely particulate gel silicas and nonionic hydrocolloids, such as carboxmethyl cellulose, sodium hydroxymethyl cellulose, hydroxyethyl cellulose, hydroxypropyl guar, hydroxyethyl starch, polyvinyl pyrrolidone, vegetable gums, such as tragacanth, agar agar, carrageenans, gum arabic, xanthan gum, guar gum, locust bean gum, carboxyvinyl polymers, fumed silica, silica clays and the like and combinations thereof. A preferred thickening agent is carrageenan available under the trade names GELCARIN® and VISCARIN® from FMC Biopolymers, Philadelphia, Pa., U.S.A. Other thickening agents or binders are polyvinyl pyrrolidone available from Noveon, Inc. Cleveland, Ohio, U.S.A. under the trademark CARBOPOL®, fumed silica under the trademark CAB-O-SIL® available from Cabot Corporation, Boston, Mass., U.S.A. and silica clays available from Laporte Industries, Ltd., London, U.K. under the trademark LAPOINTE®. The thickening agent or binder may be used with or without a carrier, such as glycerol, polyethylene glycol (PEG-400), or combinations thereof, however, when a carrier is used, up to about 5% thickening agent or binder, preferably from about 0.1% to about 1.0%, is combined with about 95.0% to about 99.9% carrier, preferably about 99.0% to about 99.9%, based on the total weight of the thickening agent/carrier combination.

Any food grade and/or pharmaceutically acceptable sweetener maybe used in the toothpaste, gels or tooth powders including saccharin, fructose, xylitol, saccharin salts, thaumatin, aspartame, D-tryptophan, dihydrochalcones, acesulfame and cyclamate salts, especially sodium cyclamate and sodium saccharin, and combinations thereof. The sweetener must be selected such that it does not promote tooth decay.

Any of the customary abrasives or polishes may be used, including those selected from the group consisting of chalk, calcium carbonate, dicalcium phosphate, insoluble sodium metaphosphate, aluminum silicates, calcium pyrophosphate, finely particulate synthetic resins, silicas, aluminum oxide, aluminum oxide trihydrate, hydroyapatite, and the like, or combinations thereof. The abrasive or polishes may, preferably be, completely or predominantly finely particulate xerogel silica, hydrogel silica, precipitated silica, aluminum oxide trihydrate and finely particulate aluminum oxide or combinations thereof. Silicas available from J. H. Huber Corporation, Havre de Grace, Md., U.S.A. under the trade names ZEOFREE® and ZEODENT® may be used in the invention.

Surfactants useful in the toothpastes or gels, are those selected from the group consisting of anionic high-foam surfactants, such as linear sodium $C_{12-18}$ alkyl sulfates; sodium salts of $C_{12-16}$ linear alkyl polyglycol ether sulfates containing from 2 to 6 glycol ether groups in the molecule; alkyl-($C_{12-16}$)-benzene sulfonates; linear alkane-( $C_{12-18}$)-sulfonates; sulfosuccinic acid mono-alkyl-($C_{12-18}$)-esters; sulfated fatty acid monoglycerides; sulfated fatty acid alkanolamides; sulfoacetic acid alkyl-($C_{12-18}$)-esters; and acyl sarcosides, acyl taurides and acyl isothionates all containing from 8 to 18 carbon atoms in the acyl moiety. Nonionic surfactants, such as ethoxylates of fatty acid mono- and diglycerides, fatty acid sorbitan esters and ethylene oxide-propylene oxide block polymers are also suitable. Particularly preferred surfactants are sodium lauryl sulfate and sacrosinate. Combinations of surfactants can be used.

Preservatives and antimicrobial agents that may be used in the toothpaste or gels include those selected from the group consisting of p-hydroxybenzoic acid; methyl, ethyl or propyl ester; sodium sorbate; sodium benzoate, bromochlorophene, phenyl salicylic acid esters, thymol, and the like; and combinations thereof. Suitable pH buffers include those selected from the group consisting of primary, secondary or tertiary alkali phosphates, citric acid, sodium citrate, and the like or combinations thereof. Wound healing and inflammation inhibiting substances include those selected from the group consisting of allantoin, urea, azulene, camomile active substances and acetyl salicylic acid derivatives, and the like, or combinations thereof.

Colorants, that is, colors, dyes, pigments and particulate substances, may be used in the toothpaste or gels. An example of a pigment is titanium dioxide (such as U.S.P. grade available from Whittaker, Clark & Daniels) to provide a bright white color. Food grade and/or pharmaceutically acceptable coloring agents, dyes, or colorants, as would be understood to one skilled in the art, can be used in these compositions, including FD&C colorants including primary FD&C Blue No. 1, FD&C Blue No. 2, FD&C Green No. 3, FD&C Yellow No. 5, FD&C Yellow No. 6, FD&C Red No. 3, FD&C Red No. 33 and FD&C Red No. 40 and lakes FD&C Blue No. 1, FD&C Blue No. 2, FD&C Yellow No. 5, FD&C Yellow No. 6, FD&C Red No. 2, FD&C Red No. 3, FD&C Red No. 33, FD&C Red No. 40 and combinations thereof.

We have found that incorporation of diglycerol in oral care compositions and chewing gum provides an enhanced long lasting smooth effect and longer flavor and cooling sensation, and that the oral care compositions comprising diglycerol maintain enhanced smoothness effect and the longer flavor and cooling sensation on the teeth and gums. While not wishing to be bound to any theory, the enhanced smoothness effect and longer flavor and cooling sensation may be the result of the size of the diglycerol molecule and its interaction with the flavoring and cooling agents after application. Diglycerol is a relatively large molecule compared to humectants traditionally used in oral care compositions, such as glycerol, and thus does not dissolve at as high of a rate as traditional humectants. Because of the size of the diglycerol molecule, it will bind the flavoring agents which may also comprise cooling agents, on the teeth and gums after application and because the dissolution rate is slower, the flavoring agent is maintained on the surface of the teeth and gums thus enhancing the effects. Diglycerol also does not absorb moisture from the gums like other humectants, such as glycerol, which may also enhance the smoothness effects of the oral care compositions.

Diglycerol provides a further advantage when used in oral care compositions in the form of clear gels. Clear gels generally have a refractive index between about 1.44 and about 1.45. The refractive index of diglycerol is 1.49 which allows for clear gel formulations with more water than formulations comprising traditional oral care humectants, such as glycerol that has a refractive index of 1.48.

Diglycerol provides a further advantage when used in sugar-free chewing gum applications. Chewing gum processing generally includes the steps of mixing together the ingredients then extruding the mass into sheets or ropes which are then cooled and shaped by rolling, sizing and cutting into individual pieces that are wrapped for presentation for sale. Usually sugar-free chewing gums present processing problems because they lack elasticity and stretching ability and thus conventional process cannot be readily used to make sugar-free chewing gum products. The inclusion of diglycerol in the humectant-system of sugar-free chewing gum imparts more elasticity to the sugar-free chewing gum formulation thereby adapting the sugar-free chewing gum composition to processing more easily by processes conventionally used for gum comprising sugar.

Accordingly, the invention encompasses an improved process of making sugar-free chewing gum having the steps of mixing ingredients of a sugar-free chewing gum, e.g. at least gum base, sugarless sweetener and the humectant system, extruding the mixture into sheets or ropes, cooling and shaping the extruded mixture by rolling, sizing and cutting the ropes or sheets and packaging wherein the improvement comprises mixing as an ingredient a humectant system having at least diglycerol preferably in an amount of about 5% to about 95% (based on the total weight of humectant material in the composition). In the improved process, the humectant may be in an amount from about 0.1% to about 25% of the composition, preferably from about 0.3% to about 6% and most preferably from about 0.5% to about 4%. Other ingredients in the process may include sugar free bulk sweeteners and/or sugarless sweeteners, such as in an amount of about 5% to about 70% by weight, flavoring agents, such as in an amount of about 0.1% to about 5% or more, and any other of the ingredients discussed herein with respect to chewing gums, except that in the improved process of the ingredients do not comprise sugar sweeteners, like those discussed herein.

EXAMPLES

The invention is further described in the following non-limiting examples. In these examples, the oral care compositions may not comprise active components or other ingredients that are not essential to the long lasting smoothness and enhanced flavoring and cooling effects unexpectedly resulting from the incorporation of diglycerol in the compositions.

Example 1

In this example, a traditional dentifrice gel formulation was made except that diglycerol was substituted for glycerol as a humectant in the composition. The dentifrice gel formulation prepared for this example had the composition set forth in Table 1.

TABLE 1

| INGREDIENT | WT % |
| --- | --- |
| Polyethylene Glycol | 3.00 |
| Carboxymethyl Cellulose | 1.20 |
| Carrageenan | 0.30 |
| Water | QS |
| Diglycerol | 37.60 |
| Sodium Benzoate | 0.20 |
| Sweetener | 0.20 |
| Colorant | 0.10 |
| Silica | 10.00 |
| Sorbitol | 30.00 |
| Silica Thickener | 0.25 |
| Flavoring | 1.00 |
| Surfactant | 1.15 |

The dentifrice gel was made by combining various separately prepared phases, as follows:

1. A first phase was prepared by dispersing carboxymethyl cellulose (CMC-12M31XP available from Hercules Incorporated, Wilmington, Del., U.S.A.) and carrageenan (GELCARIN® DG from FMC Biopolymer) in polyethylene glycol (PLURACOL® E400, from BASF, Mt. Olive, N.J., U.S.A.)
2. A second phase was prepared by combining 50 grams of water (10% of the total composition) and diglycerol (from Solvay Interox, Inc.), then dissolving saccharin and sodium benzoate (from Mallinckrodt Baker, Inc., Phillipsburg, N.J., U.S.A.), then adding colorant (FD&C Blue No. 1 dye) and heating to 60° C. The first phase was then added to the second while at 60° C. and the phases were mixed for about 20 to about 30 minutes, and then this mixture was transferred to a model LDM-1 quart double planetary mixer available from Charles Ross & Son Co., Hauppauge, N.Y., U.S.A., (referred to in this Specification as the "Ross Mixer").
3. A third phase was prepared by combining 25 grams (5% of the total composition) of ZEOFREE® 153 and 25 grams (5% of the total composition) of ZEODENT® 113 silica (from J. M. Huber Corporation).

The silica was then added with mixing over a 15 minute period to the Ross Mixer. Once the silica was added to the Ross Mixer, mixing continued for an additional 15 minutes at a vacuum of 30 inches Hg.

4. A fourth phase was made by dispersing silica thickener (CAB-O-SIL® M5 from Cabot Corporation) in sorbitol, and adding this dispersion to the Ross Mixer, at a pressure of 15 inches Hg, over a period of 15 minutes with mixing. Once the silica thickener and sorbitol dispersion were completely added to the Ross Mixer, mixing of the contents was continued for an additional 15 minutes at a vacuum of 30 inches Hg.
5. The flavoring was then added to the Ross Mixer and mixing continued for an additional 10 minutes at a vacuum of 30 inches Hg.
6. A fifth phase was prepared by dissolving surfactant (sodium lauryl sulfate, STEPANOL® WA100, from the Stepan Company) in 25 grams of water (5% of the total composition). The Ross Mixer was stopped and pressure released and the fifth phase was added to the Ross Mixer. The pressure in the Ross Mixer was then raised to 30 inches Hg and the contents were mixed for 15 minutes after which the pressure was released and the resulting dentifrice gel was transferred to storage containers.

The dentifrice gel was tested for flavoring and cooling effects by a panel of experts trained in sensory perception. Each panelist applied the dentifrice gel to the teeth and gums with a toothbrush and rinsed. A prolonged smoothness and enhanced flavoring effect on the teeth and gums was experienced.

Example 2

In this example, an opacified gel was prepared having the composition set forth in Table 2.

TABLE 2

| INGREDIENT | WT % |
| --- | --- |
| Polyethylene Glycol | 3.00 |
| Carboxymethyl Cellulose | 1.20 |
| Carrageenan | 0.30 |
| Water | QS |
| Diglycerol | 37.60 |
| Silica Thickener | 0.25 |
| Sodium Benzoate | 0.20 |
| Saccharin | 0.20 |
| Sodium Fluoride | 0.20 |
| Silica | 10.00 |
| Sorbitol | 29.35 |
| Titanium Dioxide | 0.25 |
| Flavoring | 1.00 |
| Surfactant | 1.15 |

The opacified gel was made by combining various separately prepared phases, as follows:

1. A first phase was prepared by dispersing carboxymethyl cellulose (CMC-12M31XP from Hercules Incorporated) and carragennan (GELCARIN® DG from FMC Biopolymer) in the polyethylene glycol (PLURACOL® E400 from BASF).
2. A second phase was prepared by combining 50 grams of water (10% of the total composition) and diglycerol (from Solvay Interox, Inc.), then dissolving saccharin and sodium benzoate (from Mallinckrodt Baker), then adding sodium fluoride and heating to 60° C. The first phase was then added to the second phase while at 60° C. and the phases were mixed for about 20 to about 30 minutes, and then this mixture was transferred to the Ross Mixer.
3. A third phase was prepared by combining 25 grams (5% of the total composition) of ZEOFREE® 153 and 25 grams (5% of the total composition) of ZEODENT® 113 silica (from J. M. Huber Corporation). The silica was then added with mixing over a 15 minute period to the Ross Mixer. Once the silica was added to the Ross Mixer, mixing continued for an additional 15 minutes at a vacuum of 30 inches Hg.
4. A fourth phase was made by dispersing silica thickener (CAB-O-SIL® M5 from Cabot Corporation) in sorbitol, and adding this dispersion to the Ross Mixer, at a pressure of 15 inches Hg, over a period of 15 minutes with mixing. Once the silica thickener and sorbitol dispersion were completely added to the Ross Mixer, mixing of the contents was continued for an additional 15 minutes at a vacuum of 30 inches Hg.
5. The flavoring was then added to the Ross Mixer and mixing continued for an additional 10 minutes at a vacuum of 30 inches Hg.
6. A fifth phase was prepared by dissolving surfactant (sodium lauryl sulfate, STEPANOL® WA100, from the Stepan Company) in 25 grams of water (5% of the total composition). The Ross Mixer was stopped and pressure released and the fifth phase was added to the Ross Mixer. The pressure in the Ross Mixer was then raised to 30 inches Hg and the contents were mixed for 15 minutes after which the pressure was-released and the resulting opacified gel was transferred to storage containers.

The gel was tested by an expert panel by applying to the teeth and gums using a toothbrush as described in Example 1. A prolonged smoothness and enhanced cooling and flavoring effect on the teeth and gums were experienced by the panel.

Example 3

In this example, a peppermint flavored mouth rinse gel was prepared having the composition set forth in Table 3.

TABLE 3

| INGREDIENT | WT % |
| --- | --- |
| Polyethylene Glycol | 3.00 |
| Carboxymethyl Cellulose | 0.50 |
| Carrageenan | 0.30 |
| Water | QS |
| Diglycerol | 30.00 |
| Saccharin | 0.30 |
| Licorice Extract | 0.20 |
| Silica | 15.00 |
| Pigments | 1.01 |
| Titanium Dioxide | 0.10 |

TABLE 3-continued

| INGREDIENT | WT % |
| --- | --- |
| Sorbitol | 36.20 |
| Flavoring | 2.00 |
| Surfactant | 1.15 |

The mouth rinse gel was made by combining various separately prepared phases, as follows:
1. A first phase was prepared by dispersing carboxymethyl cellulose (CMC-12M31XP from Hercules Incorporated) and carragennan (GELCARIN® DG from FMC Biopolymer) in polyethylene glycol (PLURACOL® E400 from BASF).
2. A second phase was prepared by combining 50 grams of water (10% of the total composition) and the diglycerol (from Solvay Interox, Inc.), then dissolving saccharin and licorice extract (MAGNASWEET® 120 from Mafco Worldwide, Camden, N.J., U.S.A.) and heating to 60° C.

The first phase was then added to the second while at 60° C. and the phases were mixed for about 20 to about 30 minutes, and then this mixture was transferred to the Ross Mixer.
3. A third phase was prepared by combining 50 grams (10% of the total composition) of ZEOFREE® 153 and 25 grams (5% of the total composition) of ZEODENT® 113 silica (available from J. M. Huber Corporation), 5 grams (1% of the total composition) of TIMIRON® MP-49 pigment (from EM Industries Inc., Hawthorne, N.Y., U.S.A.), 0.01 grams (0.05% of the total composition) of Mica Black pigment (from EM Industries Inc.) and titanium dioxide (U.S.P. grade from Whittaker, Clark & Daniels). This combination was then added with mixing over a 15 minute period in the Ross Mixer. Once this was added to the Ross Mixer, mixing continued for an additional 15 minutes at a vacuum of 30 inches Hg.
4. A fourth phase was made by dispersing the silica thickener (CAB-O-SIL® M5 available from Cabot Corporation) in sorbitol, and adding this dispersion to the Ross Mixer, at a pressure of 15 inches Hg, over a period of 15 minutes with mixing. Once the silica thickener and sorbitol dispersion were completely added to the Ross Mixer, mixing of the contents was continued for an additional 15 minutes at a vacuum of 30 inches Hg.
5. The flavoring was then added to the Ross Mixer and mixing continued for an additional 10 minutes at a vacuum of 30 inches Hg.
6. A fifth phase was prepared by dissolving the surfactant (sodium lauryl sulfate, STEPANOL® WA100, from the Stepan Company) in 25 grams of water (5% of the total composition). The Ross Mixer was stopped and pressure released and the fifth phase was added to the Ross Mixer. The pressure in the Ross Mixer was then raised to 30 inches Hg and the contents were mixed for 15 minutes after which the pressure was released and the resulting mouth rinse gel was transferred to storage containers.

The mouthrinse gel was tested by an expert panel trained in sensory perception. Each panelist applied the mouthrinse gel by placing a quantity of gel into the mouth, moving the gel past the teeth and gums and expectorating. The panelists were then asked to record the cooling sensation every 30 seconds for a total of 17½ minutes based on the following scale:

0–2: very low perception of cooling

2–4: medium perception of cooling

4–6: high perception of cooling.

A comparative formulation not containing diglycerol was also evaluated on the same scale. The results are set forth in FIG. 1.

Example 4

In this example, a flavored mouth rinse was prepared having the composition set forth in Table 4.

TABLE 4

| INGREDIENTS | WT % |
|---|---|
| Glycerol | 5.00 |
| Xanthan Gum | 0.12 |
| Water | 64.10 |
| Diglycerol | 15.60 |
| Saccharin | 0.10 |
| Colorant | 0.06 |
| Flavoring | 0.15 |
| Surfactant | 0.45 |
| Alcohol | 15.00 |

The mouth rinse was prepared by making a first phase by combining water and diglycerol (from Solvay Interox, Inc.) and dissolving saccharin and colorant (FD&C Blue No. 1 dye). Next, a second phase was made by dispersing the thickening agent (xanthan gum) in glycerol and then the second phase was added to the first phase. Next a third phase was prepared by combining the flavoring agent, surfactant (ethoxylated hydrogenated castor oil, CREMOPHOR® RH-40 available from BASF, Mount Olive, N.J., U.S.A.), and alcohol. The combined first and second phases were added to the third phase and the all of the phases were mixed together at ambient temperature for 5 minutes to obtain the mouth rinse.

The mouth rinse was analyzed by an expert panel and applied to the teeth and gums by placing a quantity in the mouth, moving the mouth rinse past the teeth and gums a plurality of times and expectorating. The mouth rinse provided long lasting smoothness, and enhanced cooling and flavoring effects on the teeth and gums.

Example 5

Mouth rinse formulations were prepared having the formulas set forth in Table 5. The mouth rinse formulation of Sample 5A is prepared in accordance with the invention having humectant diglycerol. Sample 5B is a comparative example having mouth rinse prepared with sorbitol as the humectant.

TABLE 5

| | WT % | |
|---|---|---|
| INGREDIENTS | Sample 5A | Sample 5B (Comparative) |
| Glycerol | 10.00 | 10.00 |
| Xanthan Gum | 0.12 | 0.12 |
| Water | 69.33 | 69.33 |
| Diglycerol | 20.00 | 0 |
| Sorbitol | 0 | 20.00 |
| Saccharin | 0.10 | 0.10 |
| Titanium Dioxide | 0.10 | 0.10 |
| Surfactant | 0.45 | 0.45 |
| Flavoring | 0.15 | 0.15 |

The mouth rinse formulations were prepared by making first phases by combining water and humectant and then dissolving the saccharin. The humectant used for Sample 5A, which was made in accordance with the invention, was diglycerol (from Solvay Interox, Inc.) and sorbitol was used as the humectant for the comparative example (Sample 5B). Next, second phases were prepared by dispersing the thickening agent (xanthan gum) in glycerol, and then the second phases were added to each first phase. Titanium dioxide (U.S.P. grade from Whittaker, Clark & Daniels) was then added to each of the combined first and second phases and mixed for 5 minutes at ambient temperature. Flavoring was added to surfactant (CREMOPHOR® RH-40 from BASF) to obtain third phases. The combined titanium dioxide and first and second phases were added to the third phases to obtain the compositions of Sample 5A and Sample 5B.

Samples 5A and 5B were evaluated by an expert panel of 10 individuals. These samples were separately applied to the teeth and gums of each expert panelist by placing a quantity in the mouth, moving the mouth rinse past the teeth and gums a plurality of times and expectorating. Water was used to rinse the mouth between application of Samples 5A and 5B. Each panelist was asked to report the total time that a cooling effect was experienced in the mouth for each sample. The average time for cooling effect experienced by the panelists was about 30 minutes for Sample 5A and about 10 minutes for sample 5B.

Example 6

Mouth rinse formulations were prepared having the formulas set forth in Table 6. The mouth rinse formulation of Sample 6A is prepared in accordance with the invention having diglycerol as the humectant, and Sample 6B is prepared in accordance with the invention with the humectant comprising both diglycerol and sorbitol. Sample 6C is a comparative example having sorbitol humectant and no diglycerol in the composition.

TABLE 6

| | WT % | | |
|---|---|---|---|
| INGREDIENTS | SAMPLE 6A | SAMPLE 6B | SAMPLE 6C |
| Glycerol | 10.00 | 10.00 | 10.00 |
| Xanthan Gum | 0.12 | 0.12 | 0.12 |
| Water | 69.08 | 69.08 | 69.08 |
| Diglycerol | 20.00 | 10.00 | 0 |
| Sorbitol | 0 | 10.00 | 20.00 |
| Saccharin | 0.10 | 0.10 | 0.10 |
| Titanium Dioxide | 0.10 | 0.10 | 0.10 |
| Surfactant | 0.45 | 0.45 | 0.45 |
| Flavoring | 0.15 | 0.15 | 0.15 |

The mouth rinse formulations were prepared by making first phases by combining water and the respective humectant for each sample then dissolving the saccharin. Diglycerol (from Solvay Interox, Inc.) was used for Sample 6A, a combination of diglycerol (from Solvay Interox, Inc.) and sorbitol was used for Sample 6B and sorbitol was used for Sample 6C. Next, second phases were prepared by dispersing the thickening agent (xanthan gum) in glycerol, and then the second phases were added to each first phase. Then, titanium dioxide (U.S.P. grade from Whittaker, Clark & Daniels) was added to the combined first and second phases and mixed for 5 minutes at ambient temperature. Next, flavoring was added to the surfactant (CREMOPHOR®) RH-40 from BASF) to obtain third phases. The combined titanium dioxide, first phases and second phases were added to the third phases to obtain the compositions of Sample 6A, 6B and 6C.

Samples 6A, 6B and 6C were evaluated by an expert panel of 10 panelists. The panelists applied each sample to the teeth and gums by placing a quantity in the mouth, moving the mouth rinse past the teeth and gums a plurality of times and expectorating. Water was used to rinse the mouth between the application of each sample. Each panelist was asked to report the total time that a cooling effect was experienced in the mouth for each sample. The average time for cooling effect experienced by the panelists was about 30 minutes for Sample 6A, about 20 minutes for Sample 6B and about 5 minutes for Sample 6C.

Example 7

A milky mouthwash, that is a mouth wash having an opaque and cloudy appearance, was made according to the invention by first making a water phase by combining 42.24 grams of diglycerol (from Solvay Interox, Inc.) and 0.30 grams of saccharin with 225.00 grams of water in a mixer and mixing for about 10 minutes at ambient temperature, then adding a thickening agent comprising 0.36 grams of xanthan gum dispersed in 15 grams of glycerol with continued mixing for about 5 minutes at ambient temperature then adding 0.30 grams of titanium dioxide (U.S.P. grade from Whittaker, Clark & Daniels) with continued mixing for about 10 minutes at ambient temperature. Separately, an oil phase was made by combining 15 grams of glycerol, 1.35 grams of surfactant (CREMOPHOR® RH-40 from BASF) and 0.45 grams of flavoring in a mixer with mixing for about 10 minutes at ambient temperature. The water phase was then combined with the oil phase in the mixer and mixing continued for about 10 minutes at ambient temperature to obtain the mouthwash composition comprising diglycerol having a cloudy and milky appearance. A long lasting cooling effect was experienced on the teeth and gums with the milky mouth rinse of this Example.

Example 8

A tinted milky mouthwash was made according to the invention by first making a water phase by combining 42.24 grams of diglycerol, 0.30 grams of saccharin and 0.06 grams of colorant (FD&C Red No. 33 dye) with 225.54 grams of water in a mixer and mixing for about 10 minutes at ambient temperature, then adding a thickening agent comprising 0.36 grams of xanthan gum dispersed in 15 grams of glycerol with continued mixing for about 5 minutes at ambient temperature then adding 0.30 grams of titanium dioxide (U.S.P. grade from Whittaker, Clark & Daniels) with continued mixing for about 10 minutes at ambient temperature. Separately, an oil phase was made by combining 15 grams of glycerol, 0.90 grams of surfactant (CREMOPHOR® RH-40 from BASF) and 0.30 grams of flavoring in a mixer with mixing for about 10 minutes at ambient temperature. The water phase was then combined with the oil phase in the mixer and mixing continued for about 10 minutes at ambient temperature to obtain the mouthwash composition comprising diglycerol having a red-tinted cloudy and milky appearance. A long lasting cooling effect was experienced on the teeth and gums with the milky mouthrinse of this Example.

Examples 9–11

Chewing gum pieces having the compositions set forth in Table 7 were prepared. Example 9 comprises about 5% diglycerol, Example 10 comprises about 15% diglycerol and Example 11 is a comparative example that comprises glycerol as the humectant and does not comprise diglycerol.

Initially, SIERRA gum base (from CAFOSA® Gum, S.A. Barcelona, SPAIN) was placed in a pan dusted with mannitol and then put in an oven at about 70° C. and allowed to soften, but not liquefy. Powdered sorbitol (P60-W from Roquette Fréres, Lesterm Cedex, FRANCE) and milled xylitol (CM50 from Xyrofin Inc. Shaumburg, Ill., USA) were placed in a separate pan with pocket formed in the center, and the maltitol syrup (MALTISWEET™ from SPI Polyols, Inc., New Castle, Del., USA) was placed in the pocket.

A conventional double sigma blade mixer was heated between about 45° C. and about 50° C., and maintained at this temperature during mixing of all the ingredients. The mixer was operated at 25 RPM when used for this example. First, the maltitol syrup, half of the sorbitol and xylitol and the softened gum base were added to the mixer and the mixer was then started. The contents of the mixer were mixed for about 2–3 minutes until the ingredients were incorporated and then the mixer was stopped. Next, the acesufame-K from Nutrinova, Somerset, N.J., USA, the rest of the sorbitol and xylitol from the pan, liquid sorbitol (70/07 from Roquette Fréres) and humectant (diglycerol from Solvay Interox in Examples 9 and 10 and glycerol in Example 11) were added to the mixer. The contents of the mixer were then mixed for about 2–3 minutes until the ingredients were incorporated and then the mixer was stopped. Next the aspartame sweetener (NUTRASWEET® Aspartame Custom Gran 100 from the NutraSweet Company, Chicago, Ill., USA) and flavor were added to the mixer and the contents were mixed for about 1–2 minutes until the ingredients were incorporated and then the mixer was stopped. The contents were then removed from the mixer and placed on a pan covered with mannitol (to prevent sticking) and the gum was hand kneaded into sheets and cut into pieces. The sugar-free chewing gum was noticed to have more elasticity than typical sugar-free chewing gum formulations. The pieces were allowed to cool for up to an hour and placed into plastic bags. The chewing gum was permitted to set for at least 24 hours prior to any taste evaluations.

Figure 2:
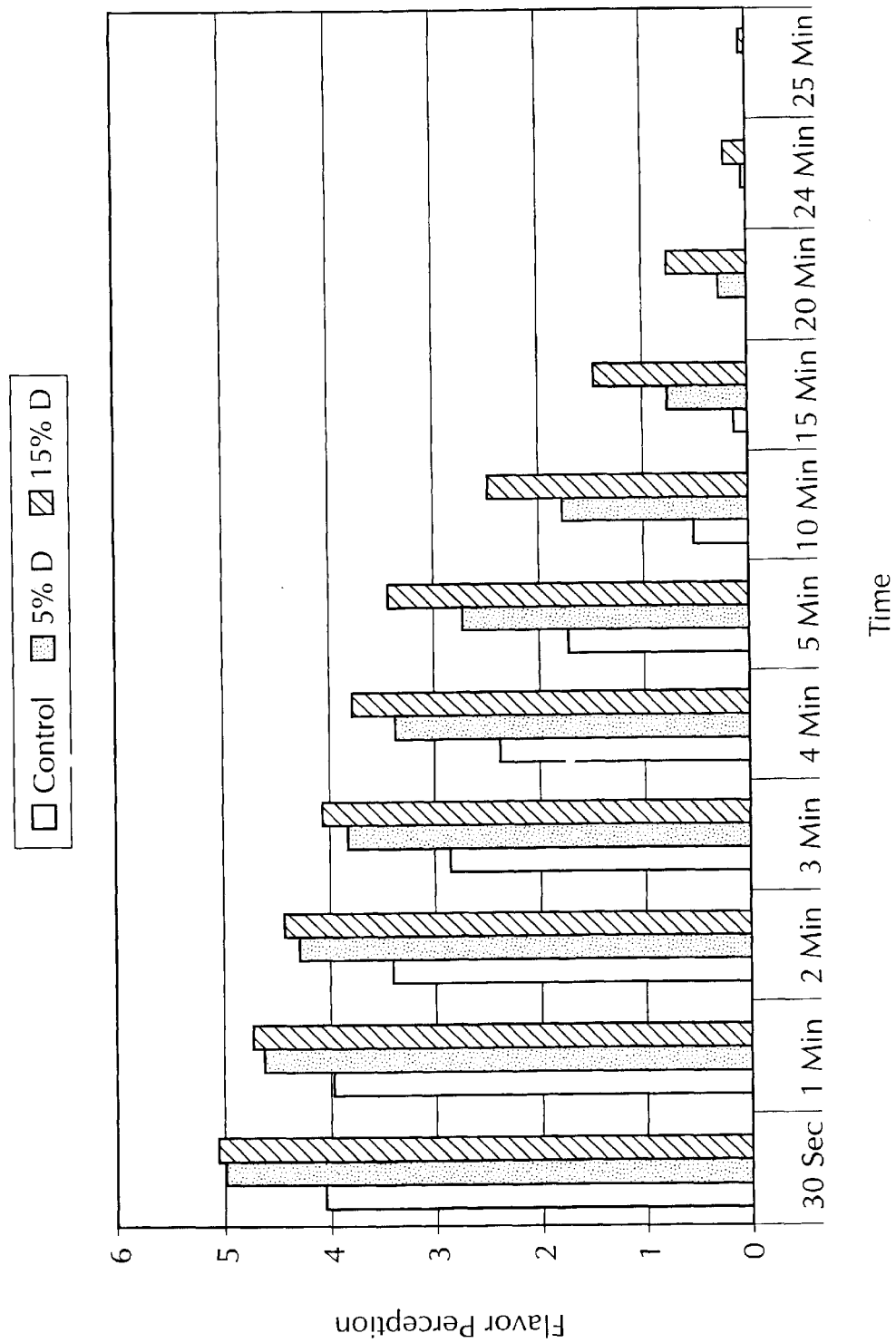
FIG. 2. is a graph depicting flavor perception over time for chewing gums comprising 5% and 15% diglycerol and no glycerol in the humectant and a comparative example wherein the humectant comprises glycerol but no diglycerol.
Figure 3:
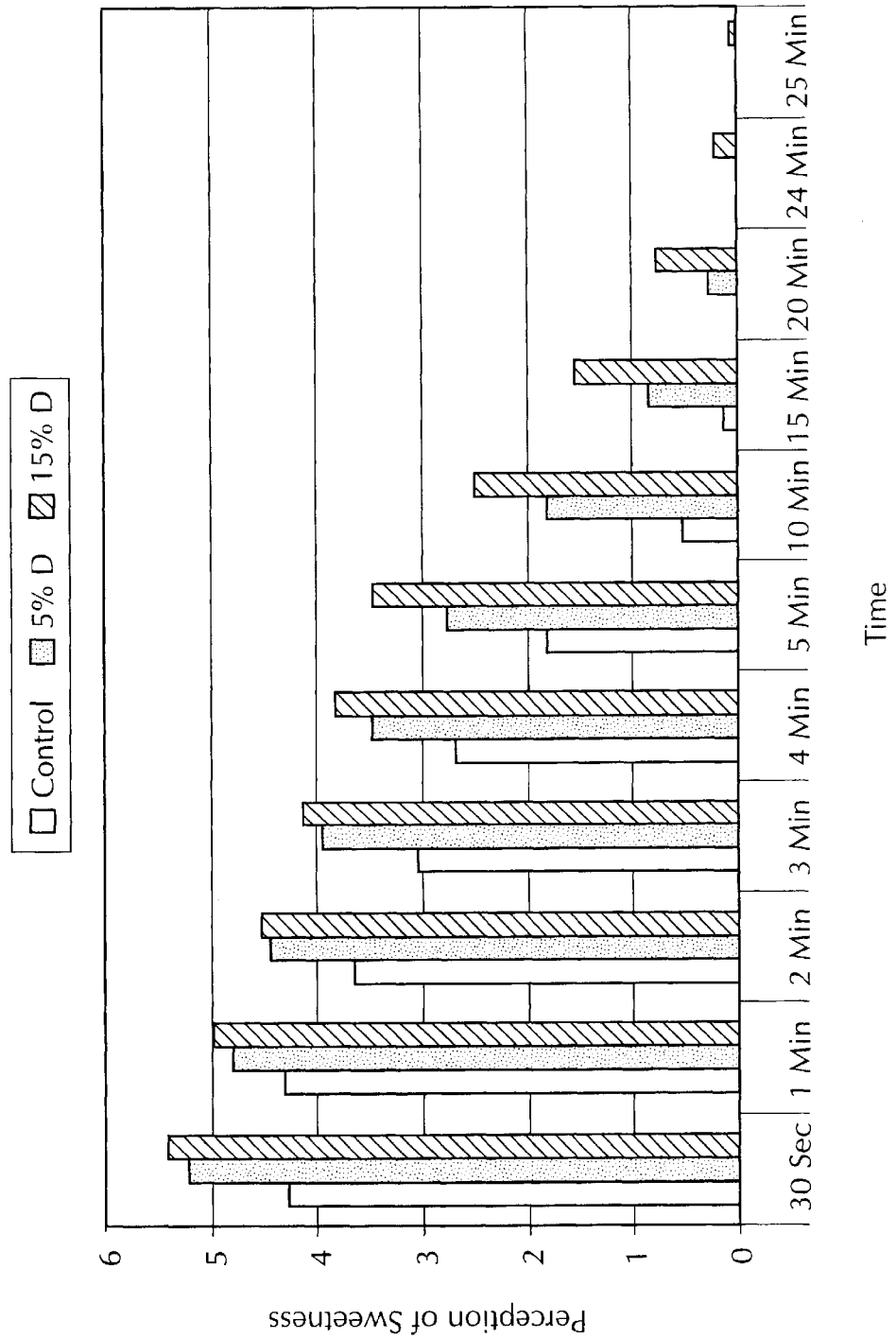
FIG. 3. is a graph depicting perception of sweetness over time for a chewing gum comprising 5% and 15% diglycerol and a comparative example having no diglycerol.

The individual pieces were then subjected to a taste test. In the taste test, each participant was asked to chew each sample of chewing gum, separately, for a total of 25 minutes and record the perception of flavor and sweetness in the mouth every 30 seconds, on a sliding scale between 0 (no perception) and 6 (high perception). The participants first chewed the comparative sample (Example 11) and then the sample comprising 5% diglycerol (Example 9) and, finally, the sample comprising 15% diglycerol (Example 10). Six people participated in the study. The taste testing results are set forth in FIG. 2 for flavor and FIG. 3 for sweetness.

TABLE 7

| INGREDIENTS | AMOUNTS (grams) | | |
|---|---|---|---|
| | EXAMPLE 9 | EXAMPLE 10 | COMPARATIVE EXAMPLE 11 |
| SIERRA GUM BASE | 250.0 | 250.0 | 250.0 |
| SORBITOL P-60W | 437.0 | 437.0 | 437.0 |
| LIQUID SORBITOL 70/07 | 150.0 | 50.0 | 160.0 |
| XYLITOL MILLED CM50 | 40.0 | 40.0 | 40.0 |
| MALTITOL SYRUP MALITSWEET 3145 | 60.0 | 60.0 | 60.0 |
| DIGLYCEROL | 50.0 | 150.0 | 0.0 |
| GLYCEROL | 0.0 | 0.0 | 40.0 |
| ASPARTAME CUSTOM GRAN 100 | 1.8 | 1.8 | 1.8 |
| ACESUFAME-K | 1.2 | 1.2 | 1.2 |
| FLAVOR | 10.0 | 10.0 | 10.0 |
| TOTALS | 1000.0 | 1000.0 | 1000.0 |

Example 12

Chewing gum pieces having the composition set forth in Table 8 were prepared. Initially, GALA gum base (from CAFOSA® Gum) was placed in a pan dusted with powdered sugar and then put in an oven at about 70° C. and allowed to soften but not liquefy. A conventional double sigma blade mixer was heated between about 45° C. and about 50° C., and maintained at this temperature during mixing of all the ingredients. The mixer was operated at 25 RPM when used for this example. The gum base and corn syrup were added to the mixer and mixed for about 2–3 minutes until the ingredients were incorporated and then the mixer was stopped. Then, half of the powdered sugar and the diglycerol were added to the contents of the mixer and mixed for about an additional 2–3 minutes until the ingredients were incorporated, and then the mixer was stopped. Finally, half of the powdered sugar and the flavoring were added to the mixer and the contents were mixed for about an additional 2–3 minutes until the ingredients were incorporated and then the mixer was stopped. The contents were then removed from the mixer and placed on a pan covered with powdered sugar (to prevent sticking) and the chewing gum was hand kneaded into sheets and cut into pieces. The pieces were allowed to cool for up to an hour and placed into plastic bags.

TABLE 8

| INGREDIENTS | AMOUNT (grams) |
|---|---|
| GALA GUM BASE | 210.0 |
| POWDERED SUGAR | 598.0 |
| CORN SYRUP 42DE 43° Bé | 180.0 |
| DIGLYCEROL | 3.0 |
| FLAVOR | 9.0 |
| TOTALS | 1000.0 |

Example 13

Chewing gum pieces having the composition set forth in Table 9 were prepared. Initially, EGARA-T gum base (from CAFOSA® Gum) was placed in a pan dusted with powdered sugar and then put in an oven at about 70° C. and allowed to soften, but not liquefy. A conventional double sigma blade mixer was heated between about 45° C. and about 50° C., and maintained at this temperature during mixing of all the ingredients. The mixer was operated at 25 RPM when used for this example. The gum base and corn syrup were added to the mixer and mixed for about 2–3 minutes until the ingredients were incorporated and then the mixer was stopped. Then, half of the powdered sugar and the diglycerol were added to the mixer and the contents of the mixer were mixed for about an additional 2–3 minutes until the ingredients were incorporated, and then the mixer was stopped. Finally, half of the powdered sugar, the citric acid and the flavoring were added to the mixer and the contents were mixed for about an additional 2–3 minutes until the ingredients were incorporated, and then the mixer was stopped. The contents were then removed from the mixer and placed on a pan covered with powdered sugar (to prevent sticking) and the chewing gum was hand kneaded into sheets and cut into pieces. The pieces were allowed to cool for up to an hour and placed into plastic bags.

TABLE 9

| INGREDIENTS | AMOUNT (grams) |
|---|---|
| EGARA-T GUM BASE | 230.0 |
| POWDERED SUGAR | 598.0 |
| CORN SYRUP 42DE 43° Bé | 150.0 |
| CITRIC ACID | 10.0 |
| DIGLYCEROL | 5.0 |
| FLAVOR | 7.0 |
| TOTALS | 1000.0 |

We claim:

1. A chewing gum composition comprising chewing gum base, sweetener, flavoring agent and from about 0.1% by weight to about 25% by weight of a humectant comprising from about 5% to 100% diglycerol by weight of the humectant wherein the dialycerol binds the flavoring agent after application to teeth and gums of a user.

2. The composition of claim 1 wherein the amount of humectant is about 0.3% by weight to about 6% by weight.

3. The composition of claim 1 wherein the sweetener comprises sugar sweeteners.

4. The composition of claim 3 wherein the sugar sweeteners are selected from the group consisting of sucrose, dextrose, maltose, dextrin, dried invert sugar, fructose, levulose, galactose, corn syrup solids and combinations thereof.

5. The composition of claim 1 wherein the sweetener comprises sugarless sweeteners.

6. The composition of claim 5 wherein the sugarless sweeteners are selected from the group consisting of sorbitol, mannitol, xylitol, hydrogenated starch hydrolysates, maltitol, isomalt, erythritol and combinations thereof.

7. The composition of claim 1 wherein the sweetener comprises artificial sweeteners.

8. The composition of claim 7 wherein the artificial sweeteners are selected from the group consisting of aspartame, saccharin, cyclamate, thaumatin, dihydrochalcones, acesulfame K compounds, sucralose, neotame, alitame, glycyrrhizin, stevioside and combinations thereof.

9. The composition of claim 1 wherein the chewing gum base comprises ingredients selected from the group consisting of elastomers, elastomer solvents, waxes, fats, fillers, softeners, plasticizers and emulsifiers.

10. The composition of claim 9 wherein the elastomers are selected from the group consisting of chicle, jelutong, sorva, nispero tunu, niger gutta, massaranduba belata, chiquibul, natural rubber, synthetic elastomers and combinations thereof.

11. The composition of claim 10 wherein the natural rubber is selected from the group consisting of smoked latex, liquid latex, smoked guayule and liquid guayule.

12. The composition of claim 10 wherein the synthetic elastomers are selected from the group consisting of polyisobutylene, isobutylene-isoprene copolymer, styrene butadiene copolymer, polyvinyl acetate, polyvinylacetate polyethylene copolymers, polyvinylacetate polyvinyl laureate copolymers and combinations thereof.

13. The composition of claim 9 wherein the elastomer solvents are selected from the group consisting of natural rosin esters, terpene resins derived from alpha-pinene, beta-pinene, and/or d-limonene and combinations thereof.

14. The composition of claim 13 wherein the natural rosin esters are selected from the group consisting of glycerol esters of partially hydrogenated rosin, glycerol esters of polymerized rosin, glycerol esters of partially dimerized rosin, glycerol esters of rosin, pentaerythritol esters of partially hydrogenated rosin, methyl esters of partially hydrogenated rosin, pentaerythritol esters of rosin and combinations thereof.

15. The composition of claim 9 wherein the waxes are selected from the group consisting of natural wax, polyethylene war, paraffin wax and microcrystalline wax.

16. The composition of claim 9 wherein the fats are selected from the group consisting of soybean oil, palm oil, sunflower oil, cottonseed oil, cocoa butter, lard, tallow and combinations thereof.

17. The composition of claim 16 wherein the fats are hydrogenated or partially hydrogenated.

18. The composition of claim 9 wherein the filler is selected from the group consisting of as calcium carbonate, magnesium carbonate, talc, dicalcium phosphate and combinations thereof.

19. The composition of claim 9 wherein the softener is glycerol monostearate or glycerol triacetate.

20. The composition of claim 1 wherein the flavoring agents comprise compounds selected from the group consisting of oil of peppermint, oil of wintergreen, oil of spearmint, clove bud oil, parsley oil, eucalyptus oil, menthol, oil of orange, oil of lemon, menthane, anethole, methyl salicylate, eucalyptol, cassia, 1-methyl acetate, sage, eugenol, oxanone, alpha-irisone, marjoram, lemon, orange, sassafras, anise, propenyl gusethol acetyl, cinnamon, vanilla, thymol, linalool, cinnamaldehyde glycerol acetal, N-substituted p-menthane-3-carboxamides, 3,1-methoxy propane 1,2-diol and combinations thereof.

21. The composition of claim 1 further comprising active ingredients, coloring agents, antiplaque agents, anticalculus agents, fluoridating agents, abrasives, polishes, preservatives, antimicrobial agents, antioxidants, emulsifiers or plasticizing agents.

22. The composition of claim 21 wherein the active ingredients are selected from the group consisting of chlorine dioxide, fluoride, alcohols, triclosan, domiphen bromide, cetyl pridinium chlorine, calcium lactate, calcium lactate salts, sodium fluoride, stannous fluoride, sodium monofluorophosphate, cetyl pyridium chloride, zinc salts, pyrophosphate, 1-hydroxyethane-1,2-diphosphonic acid, 1-phosphonopropane-1,2,3-tricarboxylic acid, azacycloalkane-2,2-diphosphonic acids, cyclic aminophosphonic acids and combinations thereof.

23. An improved process for making a sugar-free chewing gum comprising the steps of mixing a gum base, a humectant and sugarless sweetener, extruding the mixture into sheets or ropes, cooling and shaping the extruded mixture by rolling and sizing and cutting the ropes or sheets, wherein the improvement comprises mixing about 1% by weight to about 25% by weight of a humectant comprising diglycerol with the gum base and the sugarless sweetener wherein the diglycerol imparts elasticity to the sugar-free chewing gum which facilitates processing.

24. The process of claim 23 wherein the amount of the humectant is about 0.1% by weight to about 6% by weight.

25. The process of claim 23 wherein the amount of diglycerol in the humectant is about 5% to 100% diglycerol by weight of the humectant.

* * * * *